United States Patent [19]
Fahy

[11] Patent Number: 5,586,987
[45] Date of Patent: Dec. 24, 1996

[54] ANASTOMOSIS CUFF

[75] Inventor: Gregory M. Fahy, Gaithersburg, Md.

[73] Assignees: Organ, Inc.; Life Resuscitation Technologies, Inc., both of Chicago, Ill.

[21] Appl. No.: 409,705

[22] Filed: Mar. 24, 1995

[51] Int. Cl.⁶ .................................................. A61B 17/00
[52] U.S. Cl. ........................... 606/155; 606/154; 623/12
[58] Field of Search ........................... 606/150, 151, 606/153–156; 673/1, 12

[56] References Cited

U.S. PATENT DOCUMENTS

| | | | |
|---|---|---|---|
| 3,357,432 | 12/1967 | Sparks | 606/151 |
| 3,456,965 | 7/1969 | Gajewski et al. | 606/153 |
| 3,828,764 | 8/1974 | Jones | 606/153 |
| 4,553,542 | 11/1985 | Schenck et al. | 606/153 |
| 4,721,109 | 1/1988 | Healy | 606/156 |
| 5,037,428 | 8/1991 | Picha et al. | 606/153 |
| 5,139,505 | 8/1992 | Palmieri | 606/153 |
| 5,180,392 | 1/1993 | Skeie et al. | 606/155 |
| 5,254,113 | 10/1993 | Wick | 606/153 |
| 5,443,497 | 8/1995 | Venbrux | 606/151 |

*Primary Examiner*—Michael Powell Buiz
*Assistant Examiner*—Jeffrey A. Schmidt
*Attorney, Agent, or Firm*—Oliff & Berridge

[57] ABSTRACT

An anastomosis cuff for performing a vascular anastomosis procedure includes a ridge of material that extends in the radial direction. The ridge can be easily grasped with forceps or a hemostat to immobilize the cuff during an anastomosis procedure. Alternately, the anastomosis cuff can be grasped between gripping fingers of a manipulator tool designed to surround the cuff such that the ridge is trapped between and grasped by the gripping fingers.

20 Claims, 3 Drawing Sheets

ANASTOMOSIS CUFF

BACKGROUND OF THE INVENTION

The invention relates devices for performing vascular anastomosis, and more particularly to cuffs used in vascular anastomosis procedures.

Many types of surgery require vascular anastomosis. During this procedure, the cut ends of two vessels are joined together such that blood can flow through the joined vessels. Vascular anastomosis is common in transplant surgery when the vessels of the donor organ are attached to existing vessels in the patient. Vascular anastomosis is also common when a severed extremity is reattached to a patient.

FIG. 1 shows a prior art cuff 50 suitable for use in a vascular anastomosis procedure. Because the cuff 50 is cylindrical in shape, securely holding the cuff with a single pair of forceps (or a hemostat) 52 can be difficult. Because the single pair of forceps 52 only touches two points on the exterior of the cylindrical cuff 50, the cuff is free to rotate around those two points. In order to securely hold the cuff 50, a second pair of forceps (or a second hemostat) 54 must be used to grasp the cuff at a different angular orientation. By grasping the cuff with two pairs of forceps, the cuff can be securely held. Unfortunately, using two pairs of forceps is awkward and may require two hands, thus making any additional procedures difficult.

FIG. 2 shows another prior art anastomosis cuff 60, which has an extending tab 62. The extending tab 62 can be grasped by a single pair of forceps to hold the cuff relatively stable. However, because the walls of the cuff 60 are relatively thin, the extending tab 62 can flex relative to the main body of the cuff 60 when forces are applied to the cuff during an anastomosis procedure. The movement of the cuff 60 due to the flexing makes it difficult to perform the anastomosis procedure. In addition, the position of the extending tab 62 makes it difficult to grasp, and may result in interference between the tab and surrounding body tissue.

FIGS. 3A–3D illustrate a typical anastomosis procedure using a prior art cuff 50. As shown in FIG. 3A, a cuff 50 is first fitted over a severed end 72 of a vessel 70. The cuff is then grasped with one or more pairs of forceps (not shown) and the end 72 of the vessel 70 is turned inside out around the end of the cuff 50, as shown in FIG. 3B. During this procedure, the cuff 50 must be held relatively steady to allow the end 72 of the vessel 70 to be turned inside out over the cuff 50. After this is accomplished, the everted end 72 of the vessel is generally secured to the cuff with one or more sutures 74. The mating end of a second vessel 78 is then brought adjacent the everted end 72 of the first vessel 70, as shown in FIG. 3C. Next, the end of the second vessel 78 is stretched out and over the everted end 72 of the first vessel 70, as shown in FIG. 3D. The second vessel 78 is then further passed over the everted end 72 of the first vessel 70 and a circular suture 80 is then placed around both of the vessels to hold the vessels securely together and the suture is tied in a knot 82.

Because it is difficult to hold the cuff immobile during the anastomosis procedure, slippage of the cuff can occur. This is particularly problematic if the exterior of the cuff is wet, or if the forceps are held at an imperfect angle. If two pairs of forceps are used to grasp the cuff at different angles, the vessel must be accessible enough for each pair of forceps to surround the cuff from different sides. If excessive pressure is applied to a cuff in an attempt to firmly grasp the cuff, the cuff may collapse, potentially ruining the underlying portion of the vessel.

SUMMARY OF THE INVENTION

It is an object of the invention to provide a vascular anastomosis cuff that is easy to grasp and manipulate with forceps or a hemostat. A cuff according to the invention has a ridge of material extending out from the exterior surface of the cylinder in the radial direction. The ridge can be easily grasped by forceps to immobilize the cuff during an anastomosis procedure. When the cuff is used with a manipulator tool having gripping fingers designed to grasp the exterior surfaces of the cuff, the ridge can be grasped between the gripping fingers of the tool.

BRIEF DESCRIPTION OF THE DRAWINGS

Preferred embodiments of the present invention will be described with reference to the following drawing figures, wherein like features are identified with like reference numbers, and wherein.

DETAILED DESCRIPTION OF PREFERRED EMBODIMENTS

Although the specification, claims and abstract refer to vascular anastomosis, the invention is equally applicable to an anastomosis procedure that joins the ends of any type of biological duct. The use of the term vessel or vascular herein is intended to encompass not only blood vessels, but also other types of biological ducts such as a bile duct, thoracic duct or a pancreatic duct.

Figure 1:
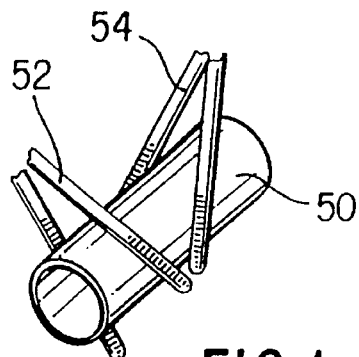
FIG. 1 is a perspective view of a prior art cuff grasped by two pairs of forceps.
Figure 2:
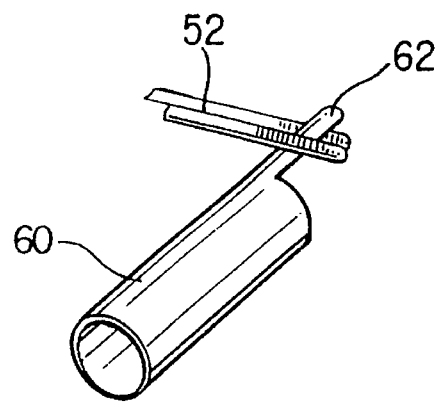
FIG. 2 is a perspective view of a prior art cuff grasped by a single pair of forceps.
Figure 3A:
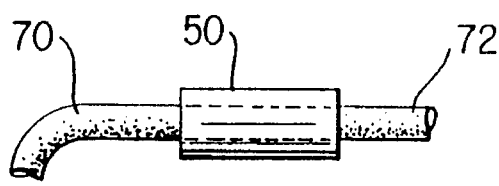
FIGS. 3A–3D illustrate a vascular anastomosis procedure.
Figure 3B:
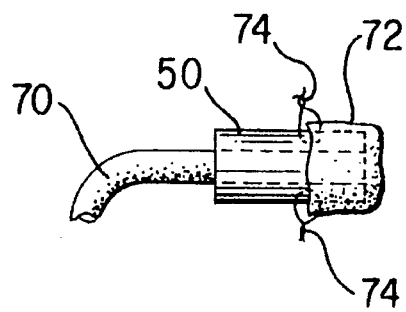
Figure 3C:
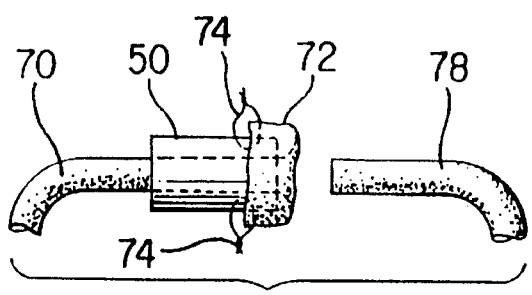
Figure 3D:
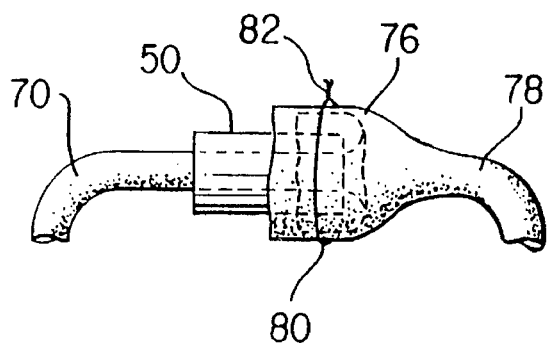
Figure 4A:
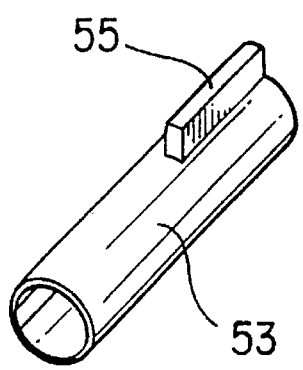
FIG. 4A and 4B are perspective views of an anastomosis cuff embodying the present invention, alone and gripped by forceps, respectively.
Figure 4B:
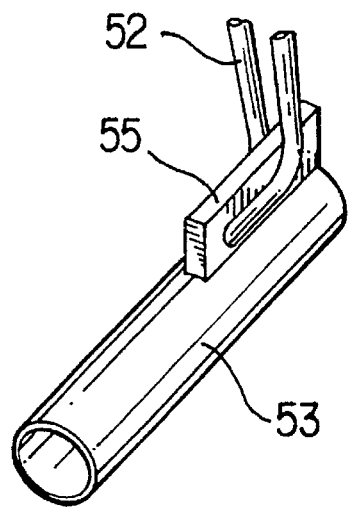

An anastomosis cuff 53 embodying the present invention is shown in FIG. 4A. The cuff 53 has a ridge of material of 55 that extends in the radial direction. As shown in FIG. 4A, the ridge 55 can be firmly grasped by forceps (or a hemostat) 52. The ridge 55 is less likely to flex relative to the main body of the cuff 53 than the extending tab 62 of the prior art cuff shown in FIG. 2. The ridge 55 thereby facilitates immobilization of the cuff during an anastomosis procedure.

When a cuff 53 having a ridge 55 is used with a manipulator tool having opposed gripping fingers designed to surround and grasp the cuff, the ridge 55 may be grasped between the gripping fingers.

Figure 5A:
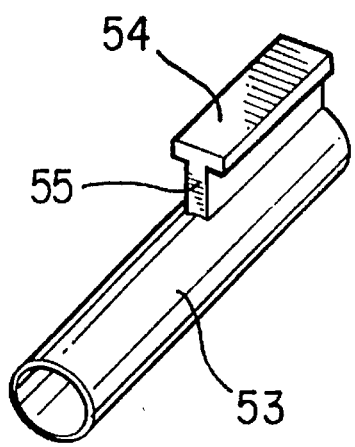
FIGS. 5A and 5B are perspective views of another anastomosis cuff embodying the present invention, alone and gripped by forceps, respectively.
Figure 5B:
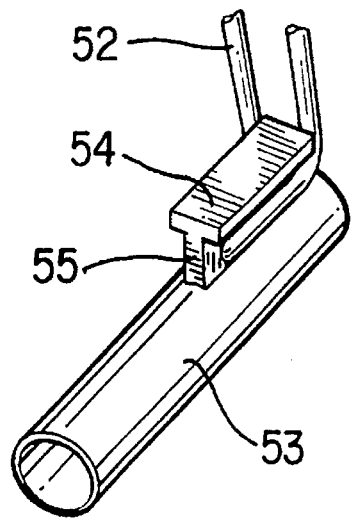

A second anastomosis cuff embodying the present invention is shown in FIG. 5A. In this embodiment, a flange 54 is included along the radial end of the ridge 55. The gripping fingers of forceps 52 used to grip the cuff 53 can be slid underneath the flange 54 to more firmly grasp the cuff 53. The flange 54 more effectively resists forces applied to the cuff 53 that might cause the axial ends of the cuff to yaw upward or downward.

Figure 6:
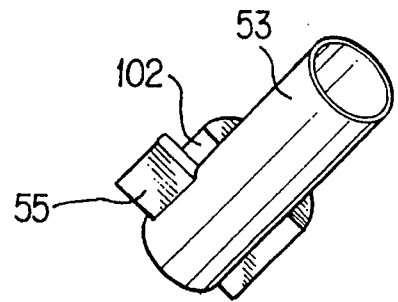
FIG. 6 is a perspective view of an anastomosis cuff embodying the present invention gripped by one gripping finger of a manipulator tool.

FIG. 6 shows a cylindrical cuff 53, inside one gripping finger of a cuff manipulator tool. Although the remainder of the manipulator tool is not shown, a mating gripping finger would close over the cuff 53 to trap the cuff 53 between the gripping fingers. When the gripping fingers 102 grasp the cuff 53, the ridge 55 is pinned between the gripping fingers 102. This will further serve to immobilize the cuff 53 during the anastomosis procedure.

Figure 7:
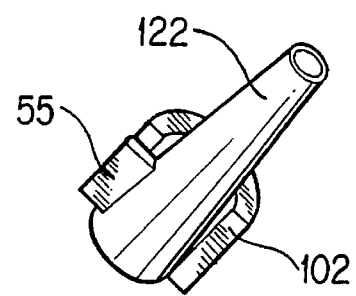
FIG. 7 is a perspective view of a conical shaped anastomosis cuff embodying the present invention gripped by one gripping finger of a manipulator tool.

As shown in FIG. 7, a conical shaped cuff 122 having a ridge 55 can also be grasped by the gripping fingers 102 of a manipulator tool. Although the insides of the gripping fingers 102 do not conform to the conical shape of the cuff 122, the ridge 55 will be grasped between the gripping fingers 102 to immobilize the cuff 122 during the anastomosis procedure.

Figure 8A:
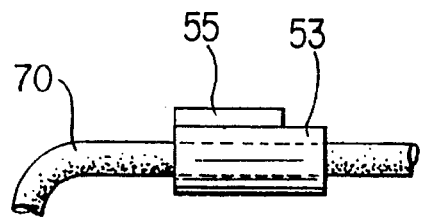
FIGS. 8A–8C illustrate a vascular anastomosis procedure using an anastomosis cuff embodying the present invention.
Figure 8B:
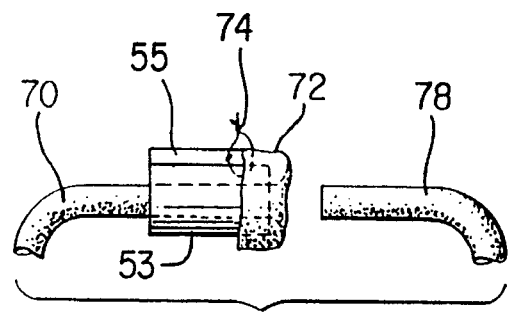
Figure 8C:
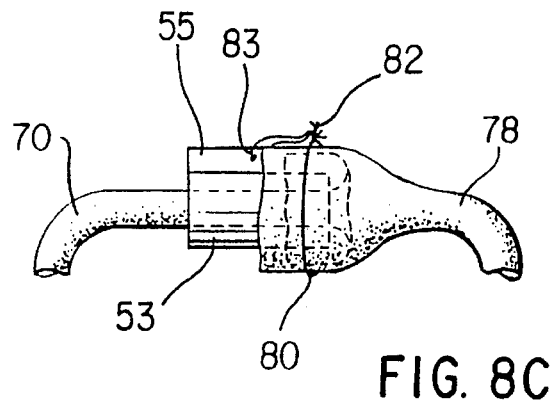

The basic anastomosis procedure using a cuff embodying the present invention is shown in FIGS. 8A–8C. A cuff 53 having a ridge 55 is first placed over a vessel 70, as shown in FIG. 8A. The end 72 of the vessel 70 is then turned inside out over the end of the cuff 53, as shown in FIG. 8B. During this procedure, the cuff 53 will be gripped by either forceps, a hemostat, or a manipulator tool having opposed gripping fingers. For ease of illustration, the manipulator tool is not shown in FIGS. 8A–8C. The everted end 72 of the vessel 70 may be sutured to the ridge 55 with one or more sutures 74 as shown in FIG. 8B. Suturing the everted end 72 to the ridge 55 eliminates the need to put a suture through the wall of the cuff to immobilize the everted end 72, as is done with a prior art cuff. The mating vessel 78 is then brought adjacent the everted end 72 of the first vessel 70. The end of the mating vessel 78 is passed over the everted end 72 of the first blood vessel 70, as shown in FIG. 8C. A circular suture 80 is placed around the mated vessels and is tied off in a knot 82. To further immobilize the mated ends of the vessels, the circular suture 80 can be tied to the ridge 55 on the cuff 53, forming knot 83.

A cuff embodying the present invention may be formed of a biologically inert material so that the cuff remains permanently in place after the procedure. Alternately, the cuff may be formed of a resorbable material so that after the ends of the vessel have grown together, the cuff will dissolve away. Furthermore, various sized cuffs may be produced to conform to various sized blood vessels or biological ducts. A surgeon could select the optimal cuff size after determining the sizes of the vessels to be joined.

While this invention has been described in conjunction with specific embodiments thereof, it is evident that many alternatives, modifications and variations will be apparent to those skilled in the art. Accordingly, the preferred embodiments of the invention, as set forth herein, are intended to be illustrative and not limiting. Various changes may be made without departing from the spirit and scope of the invention as defined in the following claims.

What is claimed is:

1. A cuff suitable for use in an anastomosis procedure, comprising:

a hollow portion having a length extending in a longitudinal axial direction of the cuff and a continuous inner surface; and a non-annular outwardly extending ridge directly connected on an exterior wall of the hollow portion, the non-annular outwardly extending ridge having a planar portion that extends along the exterior wall of the hollow portion in a direction parallel to the longitudinal axial direction such that the ridge is graspable to immobilize and position the cuff.

2. The cuff of claim 1, wherein the ridge extends in the longitudinal axial direction for less than the entire length of the cuff.

3. The cuff of claim 2, wherein the hollow portion has a cylindrical shape.

4. The cuff of claim 3, wherein the ridge is monolithically formed with the hollow portion.

5. The cuff of claim 3, wherein the ridge is formed separately from the hollow portion and is attached to the exterior wall of the hollow portion.

6. The cuff of claim 1, wherein the hollow portion has a cylindrical shape.

7. The cuff of claim 1, wherein the hollow portion has a conical shape.

8. The cuff of claim 1, wherein the ridge is monolithically formed with the hollow portion.

9. The cuff of claim 1, wherein the ridge is formed separately from the hollow portion and is attached to the exterior wall of the hollow portion.

10. The cuff of claim 1, wherein a vessel is passable through the hollow portion.

11. The cuff of claim 10, wherein an interior diameter of the hollow portion is between approximately 0.5 mm and approximately 1 cm.

12. The cuff of claim 11, wherein an outer diameter of the hollow portion is between approximately 0.6 mm and approximately 1.1 cm.

13. The cuff of claim 1, wherein the ridge is pierceable by a suture needle.

14. The cuff of claim 1, wherein the cuff is formed of a biologically inert material.

15. The cuff of claim 1, wherein the cuff is formed of a resorbable material.

16. The cuff of claim 1, further comprising a flange on the radial end of the ridge.

17. The cuff of claim 1, wherein the ridge extends along the exterior wall along a line substantially parallel to a longitudinal axis of the hollow portion.

18. A cuff suitable for use in an anastomosis procedure, comprising:

a hollow portion having a length extending in a longitudinal axial direction of the cuff and a continuous inner surface; and a non-annular outwardly extending ridge directly connected on an exterior wall of the hollow portion, the non-annular outwardly extending ridge having a flange on a radial end thereof, the ridge extending along the exterior wall of the hollow portion and being graspable to immobilize the cuff.

19. The cuff of claim 18, wherein the ridge extends in the longitudinal axial direction.

20. The cuff of claim 18, wherein the hollow portion has a cylindrical shape.

* * * * *